United States Patent
Levin et al.

[11] Patent Number: 6,114,703
[45] Date of Patent: Sep. 5, 2000

[54] HIGH RESOLUTION SCINTILLATION DETECTOR WITH SEMICONDUCTOR READOUT

[75] Inventors: Craig S. Levin, Santa Monica; Edward J. Hoffman, Los Angeles, both of Calif.

[73] Assignee: The Regents of the University of California, Oakland, Calif.

[21] Appl. No.: 08/955,069

[22] Filed: Oct. 21, 1997

[51] Int. Cl.[7] .................................................. G01T 1/20
[52] U.S. Cl. ................................ 250/367; 250/370.11
[58] Field of Search .............................. 250/370.11, 367

[56] References Cited

U.S. PATENT DOCUMENTS

| | | |
|---|---|---|
| 4,029,964 | 6/1977 | Ashe . |
| 4,100,413 | 7/1978 | Inbar et al. . |
| 4,107,534 | 8/1978 | Piltingsrud . |
| 4,110,621 | 8/1978 | Horn . |
| 4,143,271 | 3/1979 | Klein et al. . |
| 4,220,860 | 9/1980 | Carlson et al. . |
| 4,267,453 | 5/1981 | Kieboom et al. . |
| 4,437,160 | 3/1984 | Blum . |
| 4,455,616 | 6/1984 | Inbar . |
| 4,658,141 | 4/1987 | Wilt et al. . |
| 4,672,207 | 6/1987 | Derenzo . |
| 4,675,526 | 6/1987 | Rogers et al. . |
| 4,845,363 | 7/1989 | Akai ........................................ 250/368 |
| 5,013,921 | 5/1991 | Bruening et al. .................. 250/370.11 |
| 5,091,650 | 2/1992 | Uchida et al. . |

FOREIGN PATENT DOCUMENTS

| | | | |
|---|---|---|---|
| 58-182573 | 10/1983 | Japan ............................... | 250/370.11 |
| 2-59694 | 2/1990 | Japan ............................... | 250/370.11 |

OTHER PUBLICATIONS

Levin and Hoffman, "Investigation of a New Readout for High Resolution Scintillation Crystal Arrays Using Photodiodes," *IEEE Transactions on Nuclear Science*, vol. 44, No. 3, Jun. 1997, pp. 1208–1213.

*Primary Examiner*—Constantine Hannaher
*Attorney, Agent, or Firm*—Koppel & Jacobs; Michael J. Ram

[57] ABSTRACT

A novel high resolution scintillation detector array for use in radiation imaging such as high resolution Positron Emission Tomography (PET) which comprises one or more parallelepiped crystals with at least one long surface of each crystal being in intimate contact with a semiconductor photodetector such that photons generated within each crystal by gamma radiation passing therethrough is detected by the photodetector paired therewith.

18 Claims, 7 Drawing Sheets

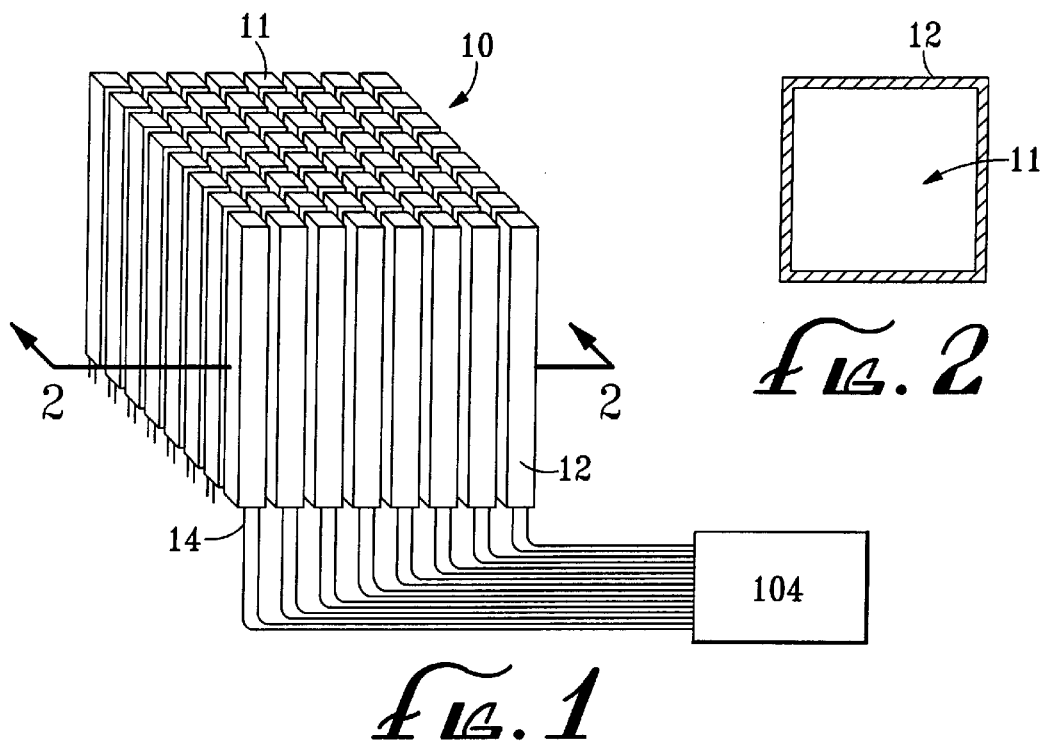
FIG. 1
FIG. 2
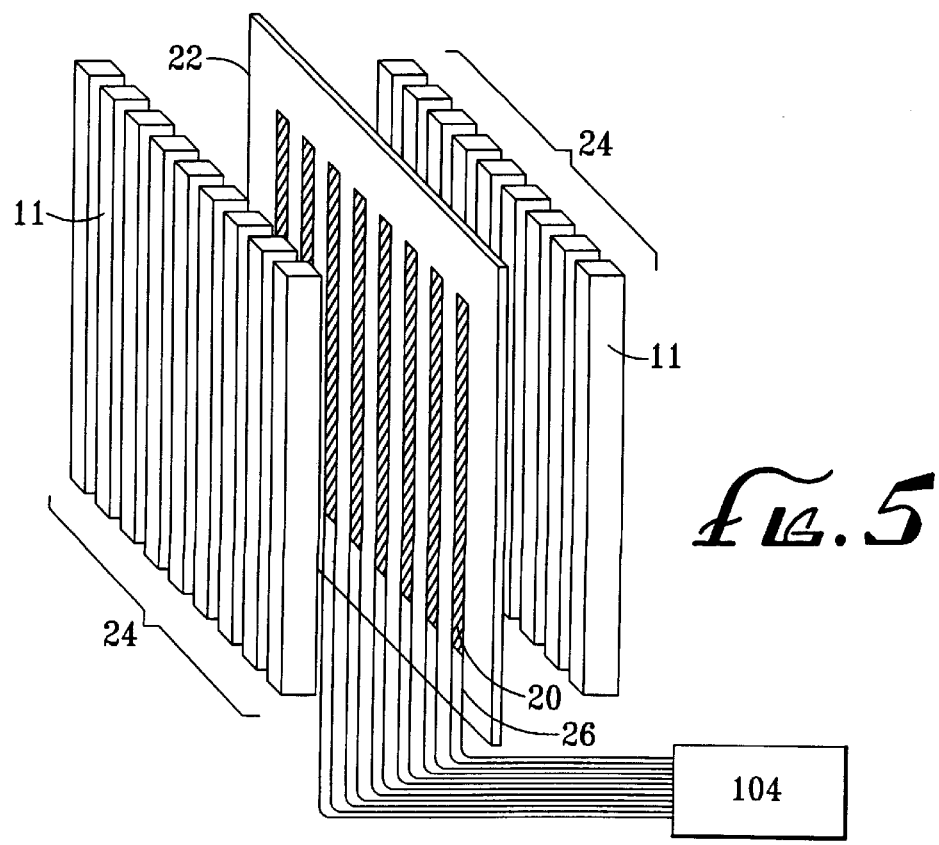
FIG. 5

HIGH RESOLUTION SCINTILLATION DETECTOR WITH SEMICONDUCTOR READOUT

This invention was made with Government support under Grant Nos. CA-56655 and CA-61037, awarded by the National Institutes of Health and DOE Contract No. DE-FC03-87ER60615, awarded by the Department of Energy. The Government has certain rights in this invention.

BACKGROUND

This invention relates to scintillator crystals and more particularly to scintillation crystal arrays, and a novel method for improving the detection, count efficiency and analysis of penetrating radioactive emissions. Because of the resulting potential improvements in spatial, spectral and temporal resolutions, the concept may be particularly useful in Positron Emission Tomography (PET).

Scintillation crystals are commonly used in non-invasive medical diagnostic techniques which utilize radiation emitting materials. These crystals are noted for their ability to emit pulses of visible light when ionizing radiation, such as gamma radiation, passes therethrough and interacts with atomic nuclei in the crystal. The pulses of emitted light (photons) are then detected by a photodetector device such as a photomultiplier tube (PMT) or a semiconductor photodiode (SPD). The effectiveness of the detector in diagnostic procedures depends on the ability to see and quantify the crystal light flashes with high spatial, spectral, and temporal precision. This in turn is dependent on brightness and rapidity of the generated flash which are functions of the type and geometry of the scintillation crystal.

The state-of-the-art PET gamma-ray detector used in commercial nuclear medicine cameras utilize a two-dimensional, discrete or pseudo-discrete array of long, narrow scintillation crystals which are coupled at a small end to PMTs with the opposite small end directed toward the gamma-ray source. The crystals are preferably long for high gamma-ray stopping power and narrow for high spatial resolution. An intermediate optical coupling medium is necessary in these designs at the scintillation crystal/PMT interface. Crystal surfaces in these designs are treated and coated with reflectors to preferentially direct light through internal reflections into the PMT located at one small end of the scintillation crystal. These prior art cameras typically quantify the scintillation light which reaches the small end of the scintillation crystal.

U.S. Pat. No. 5,091,650 describes a typical PMT/scintillator array arrangement. Since individual PMTs are expensive and rather bulky, the unit is usually constructed such that the number of scintillation crystals in a PET detector array is much larger than the number of PMTs used to read the light emissions. This scheme is termed "multiplexing." Typically, only four PMTs are required for one detector array unit, and an appropriate weighted mean of the 4 PMT signals determines the position of an event. Due to this multiplexing, there is a limit to the number of crystals in an array that can accurately be decoded by a given number of PMTs. This limits how narrow the crystals, or equivalently, how great the position resolution can be. For discrete crystal designs, one PMT per crystal is preferred, which is difficult for an array of narrow crystals because of size limitations of the PMT.

Another limitation in the standard PET detector design is that significant losses of scintillation light occur due to photon interactions with the crystal surfaces or reflective coatings on those surfaces. The results is that only a fraction of the scintillation light produced in the crystal reaches the photodetector. This light loss problem associated with standard photodetector readout at the end of the scintillating crystal worsens as the crystal is made narrower and longer or has unpolished side surfaces. This light loss problem together with the low quantum efficiency of the PMT photocathode for detecting the scintillation light produced limits the count efficiency and signal-to-noise ratio of both the crystal decoding scheme used to position and time a gamma-ray event, and the energy (spectral) resolution required to reduce gamma-ray scatter. Good scatter reduction is an important factor for improving image contrast between true structures of interest and the background present in the resulting PET images.

An additional related problem associated with the conventional end readout is that the light collection efficiency depends on the location within the crystal where light was created and thus, where the radiation interacted. This factor degrades the energy resolution. Also, there is roughly a 10–15% light loss at the interface between the crystal and PMT due to index of refraction mismatches, further degrading the signal to noise ratio.

As a result, commercially available PET detector arrays are bulky because of the PMT and inefficient because a significant portion of scintillation light generated never reaches the photodetector. This worsens the signal-to-noise ratio and count efficiency of conventional PMT-based PET detector designs and constrains the ultimate spatial, energy, and timing resolution available. Because of the use of PMTs, these designs are also very costly.

SUMMARY

The present invention overcomes the above limitations with the use of unique combinations of semiconductor photodetectors (SPD) and scintillation crystals to efficiently detect gamma-ray (or any other form of penetrating radiation) induced light emission.

The invention embodies a novel design for a gamma-ray detector or camera for either detection, spectroscopic or imaging uses. The invention replaces the bulky and expensive PMTs by applying SPDs to the crystals in a manner that eliminates or reduces the need for polishing or reflective coatings required by the prior art. Also, the invention improves the amount of light measured from a scintillation event while maintaining high spatial resolution. Improved light detection leads to improved spectral (energy) and temporal (time) resolution. For example designs embodying features of the invention incorporate a single scintillator crystal or an array of scintillator crystals, each of which has a SPD fabricated or mounted directly onto one or more large surfaces of each crystal. In a particular embodiment each scintillation crystal is totally encapsulated within a respective photodetector. An alternative to total encapsulation is to position the photodetector on or adjacent to one or more of the long sides of the scintillation crystal as opposed to the end of the crystal as in the prior art. In this case it is desirable to apply reflective coatings to those sides of the crystal not in contact with the SPD.

The primary application for utilizing this invention is in Nuclear Medicine Imaging (NMI), such as gamma-ray cameras (Single Photon Emission Computed Tomography, (SPECT) or Planar Imaging) or Positron Emission Tomography (PET), although other applications may utilize the invention. Any type, shape or size of scintillator may be used. However, for the NMI applications, the configuration will most likely be a close-packed, two-dimensional array of inorganic scintillation crystals, which are long, thin and right-rectangular parallelepipeds. Any type of high sensitivity SPD can be used provided that it is thin enough to fit in between crystals without introducing additional significant dead area between crystals.

The most relevant application is in high resolution Positron Emission Tomography (PET), where it is critical to monitor with high precision, the gamma-ray activity of small radio-labeled structures within living subjects. Applications of high resolution PET include pharmaceutical and radio-pharmaceutical development, oncology, gene therapy and neuroscience.

DRAWINGS

These and other features, aspects and advantages of the present invention will become better understood with reference to the following description, appended claims, and accompanying drawings, where:

FIG. 1 is a perspective view of a two dimensional array of scintillating crystals with each crystal encapsulated by a semiconductor photodetector.

FIG. 2 is a cross section of a single crystal from the array of FIG. 1 taken along line 2—2.

FIG. 5 is an expanded view of an alternative arrangement for reading the amount of photons generated by a portion of an array of scintillating crystals (only 2 crystal planes are shown).

DESCRIPTION

Figure 3:
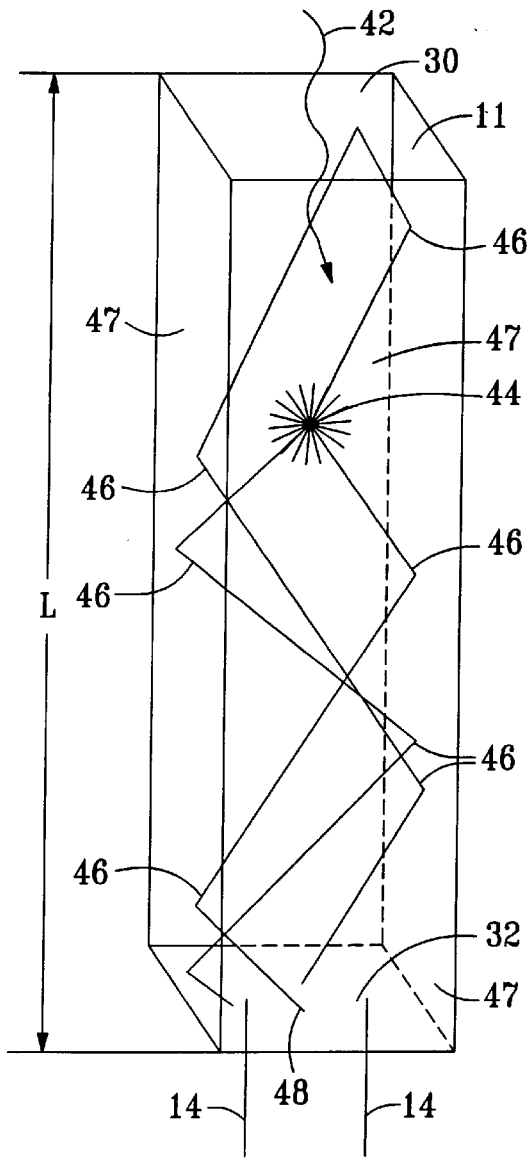
FIG. 3 is a schematic transparent representation of the prior art configuration of a single scintillating crystal for detecting photons generated by gamma radiation entering the small end of crystal.

Semiconductor photodetectors such assilicon photodiodes (SPD), together with previously developed readout electronics, are a significant low cost alternative to PMTs. In addition, because the SPD is highly compact, the development of a high resolution, low dead area scintillation detector array is simplified, and multiplexing of scintillation crystals onto PMTs is unnecessary.

Readout schemes not available to bulky PMTs, are readily available to SPDs. Prior devices have utilized photodetectors applied to the small end of long, narrow scintillation crystals with said small end being located opposite the similarly sized surface of the other small end of the crystal where the incident radiation enters this crystal. Thin SPDs can be configured onto one or more of the large faces of the long and narrow crystals, or possibly fabricated to completely cover all faces of each crystal within an array. Due to reduced crystal surface interactions that light photons encounter and a shorter photon travel path to the photodetector with this new readout geometry, light losses are reduced and the amount of light detected by the SPD is significantly higher than for the conventional PMT design. In addition, there is no dependence of the light signal on where the radiation interacted in the crystal, as occurs with small end readout. This improves the signal-to-noise ratio for detection of a given scintillation event.

If the semiconductor photodetector is actually fabricated on the crystal rather than being a separate unit placed next to the crystal face, the use of an optical coupling compound is avoided, thereby further reducing or eliminating light losses at that interface as well as the cost. However, since the SPD noise increases with its total area, this arrangement favors narrow crystals.

Another discovered benefit of the photon collection scheme embodying feature of the invention is that the amount of light detected is essentially independent of crystal length, width, surface treatment or the location of the gamma-ray interaction within the crystal. This is a result of the photodetector covering substantially all of the length of at least one side of the scintillating crystal, which significantly improves light collection compared to collecting light from the crystal end.

The lack of independence on crystal width opens the possibility of using narrower crystals for finer (higher)

position resolution. In fact, as discussed above, because of the SPD device noise, this design actually favors narrow crystals. Because the signal is not dependent on crystal surface treatment, this new construction does not require crystal polishing and the application of reflective coating can be reduced or eliminated, thereby reducing manufacturing costs.

Another benefit of replacing PMTs with silicon photodiodes is that the inherent quantum efficiency for visible light in silicon is more than a factor of 3 higher than the bialkali photocathode of the PMT, which will improve light detection efficiency.

The invention relates to scintillator crystals and arrays and more particularly to an improved construction for detecting photons generated within a scintillation crystal. Scintillator arrays are principal components of systems for imaging the distribution of radio-pharmaceuticals injected into a patient by detecting the gamma-rays that escape the absorbing medium of the body. Certain tissue within the body absorbs a particular radiopharmaceutical at a differential rate producing a distribution of the radioisotope. Counting the gamma-ray emissions with a tomographic array of detectors enables the creation of an image showing a spatial distribution of how the organs and tissue utilize a particular radiopharmaceutical.

In a first embodiment, a solid state photodetector (SPD) is formed directly on long faces of each crystal in a scintillation crystal array without an intermediate optical coupling compound at the scintillation crystal/SPD interface. Formation of the SPD is by common techniques such as crystal growth from solution or melt, chemical vapor deposition, or molecular beam epitaxy.

The SPD coating is preferably applied to at least one large face of the crystal, but may be applied to all surfaces. Those surfaces not coated with the SPD are preferentially coated with a reflective material. Photons generated within the scintillation crystal strike the photodetector where they are then collected and the resulting electrical signal measured. For convenience, the photodetector leads are configured at the small end of each long and thin scintillation crystal.

By fabricating the semiconductor photodiode directly upon one of the longer surfaces of a scintillation crystal the need for an optical coupling compound is eliminated thus further reducing light losses. FIG. 1 depicts an 8×8 array 10 of coated scintillation crystals. As shown in FIG. 2, each scintillation crystal 11 of the scintillation crystal array 10 is encapsulated by photodetector 12. Because the photodetector 12 material is gamma-ray transparent, it can be applied to completely surround or encapsulate a respective scintillation crystal 11 on all six faces for maximum scintillation light collection (i.e., trap all the light emitted from the crystal). Photodetector leads 14, are positioned at one end of the encapsulated scintillation crystal. Means 104 for recording scintillation radiation are connected thereto.

It is desired that the space between each encapsulated photodetector be small, for example less than about <250 μm to minimize dead area between each crystal.

It is also contemplated that the photodetector may be applied separately to each face of each crystal in the array. Alternatively, the invention contemplates that less than complete coverage may be used, i.e. less than all six faces of the crystal need be covered. This would reduce device complexity and electronic noise which increases with the total SPD area used. In such event it is recommended that the faces chosen for coverage by the SPD be those with the largest area for maximum light collection (side faces preferred over end faces). However, at least one long surface should be covered by the SPD.

For various reasons it may be preferred to only fabricate the SPD onto one small end for end light readout similar to the prior art. The only advantage in this case over prior art is that no optical coupling is necessary, and light losses at the crystal/photodetector boundary are either reduced or eliminated.

Figure 14:
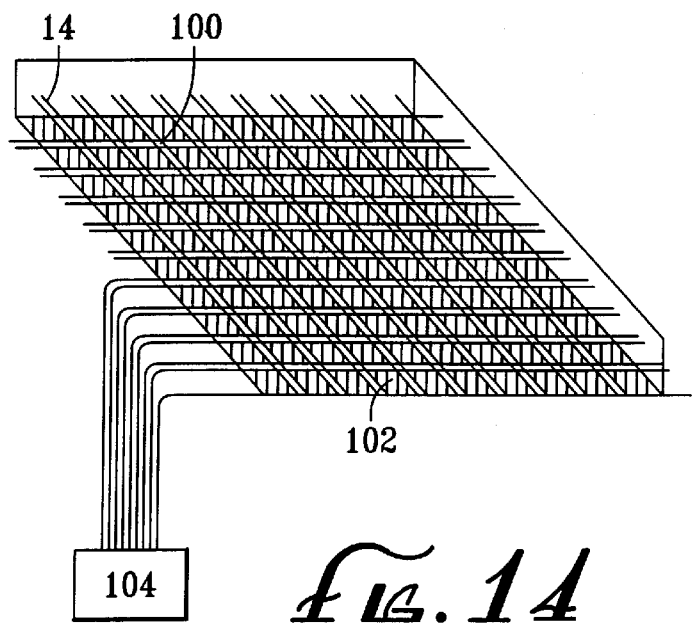
FIG. 14 is a schematic representation of a continuous scintillation crystal with SPD pixels directly fabricated onto the crystal in a 10×10 square pattern.

For a scintillation camera that utilizes a continuous large crystal 100 rather than an array of discrete crystals, an alternative is to fabricate a two-dimensional array of SPD pixels 102 directly onto the large face of that crystal 100. Means 104 for recording scintillation radiation are connected thereto. This concept is depicted in FIG. 14. The advantage over prior art for this design is the reduction of light loss by the avoidance of an optical coupling compound. An example of this is a silicon P-I-N photodiode pixels fabricated directly onto Thallium-doped Cesium Iodide (CsI (Tl)). The emission wavelength of CsI(Tl) matches well with the absorption spectrum of silicon.

A further embodiment of the invention, shown in FIG. 5 utilizes commercially existing solid state photodetectors in the form of strips 20 on very thin (<100 μm) substrate panels 22. Panels 22 are placed between multiple crystal planes 24 with each strip contacting the respective face of the scintillation crystal directly or through the use of an optical coupling medium/adhesive (not shown). SPD leads 26 are positioned adjacent to each scintillation crystal near the base. In this case, surface not in contact with a photodetector require a reflective coating. A suitable array would have multiple alternating crystal planes 24 and substrate panels 22.

Figure 7:
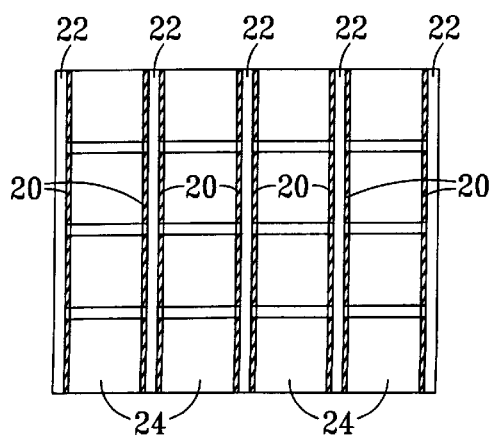
FIG. 7 is a cross sectional view taken across a 4×4 crystal array with photodetectors between crystal planes.

While a photodetector against only one surface of the crystal plane 24 is visible in FIG. 5, it is recognized that the detectors may be formed on both surfaces of the panels 22 so that, in the case of multiple alternating planes 24 and panels 22 two long surfaces of the crystal are in contact with the SPD element. In this case light is collected from a long surface from each of the two planes 24. FIG. 7 is a cross section in a 4×4 array with light collected from 2 parallel long surfaces of each plane 24. We note that the noise per crystal will be higher in this latter embodiment, since the noise from two SPDs will be present.

A disadvantage of these latter embodiments is that a substrate 22 is required on which to form the photodetector 20, which undesirably increases the thickness of the gamma-ray insensitive region of the array. It may thus be desirable to apply a "bare" SPD to each crystal which is formed by stripping the semiconductor from the substrate backing.

Figure 15:
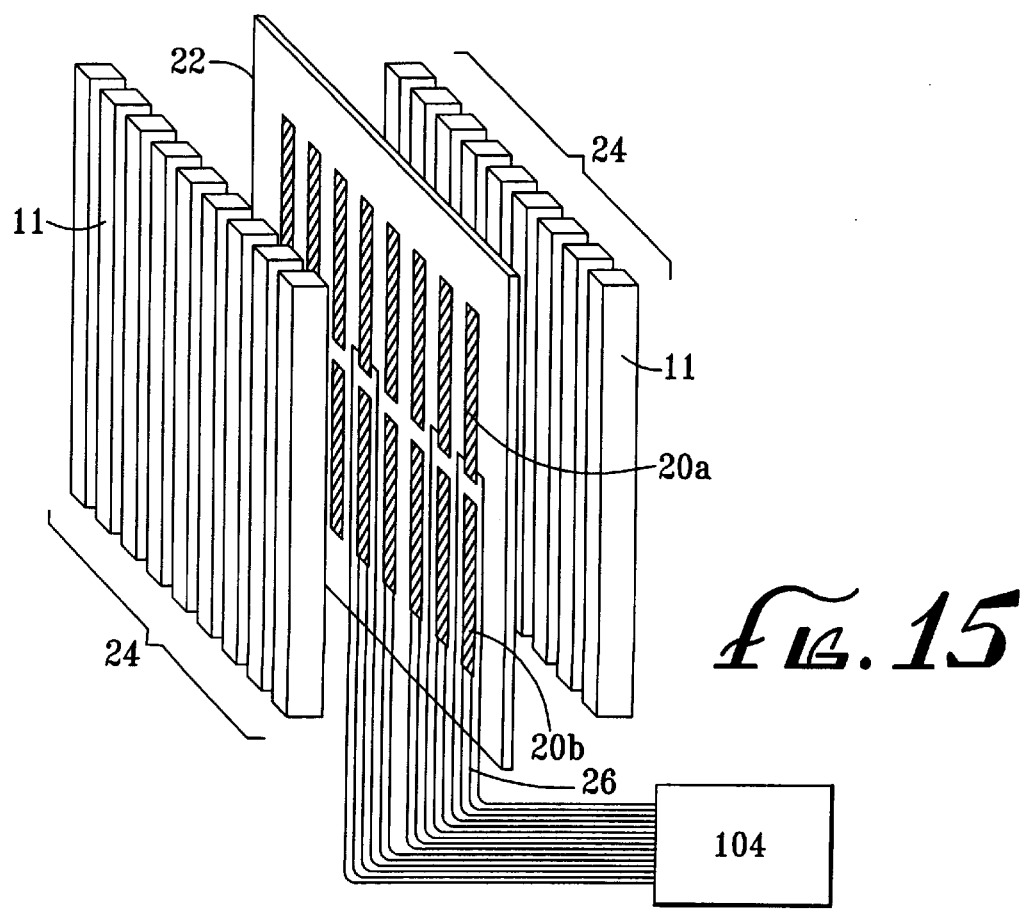
FIG. 15 is an expanded view of a further alternative arrangement of FIG. 5 for reading the location within a crystal of scintillation by use of segmented SPDs. For clarity, all of the wire connections to the scintillation recorder are not shown.

We also note, if information is desired on the depth within the crystal that the gamma-ray interacted, the SPD 12 applied to each crystal face may be appropriately segmented into portions 20a, 20b, etc as shown in FIG. 15, thereby allowing the determination of the location of brightest point or the mean location of the created light within the crystal. An alternative is to use a continuous readout with a resistive charge division along the length of the crystal using appropriate resistive electrodes on the SPD front and back faces. A third alternative is to segment the crystal and determine which crystal segment was hit by spectral or temporal (pulse shape/height discrimination) analysis. The success of any of these "depth of interaction" schemes depends on the signal to noise ratio for the particular method used.

The application of the invention can best be described by comparison to the prior art. FIG. 3 is a schematic representation of a single scintillating crystal 11 arranged in the manner used in prior art PET discrete crystal array designs. Gamma-rays enter the upper end 30 of the crystal 11 and photons 46 are created from gamma-ray interaction 44 with an atomic nucleus within the crystal. The photons 46 interact with the crystal surfaces and reflective coating 47 on the walls of the crystal 11 and, the majority of the light is reflected within the crystal. The photons which reach the bottom end 32 of the crystal 11 are detected by a photodetector 48 at the bottom end 32. The number of potential lossy surfaces optical photons will interact with in a given crystal before detection at the bottom end 32 will depend on the ratio of the length, L, to the cross-sectional area, A of the crystal 11, and the conditions of the surfaces. An optical coupling medium (not shown) is also required at the crystal 11/detector 48 interface at the bottom of the crystal. Due to high number of potential lossy reflections optical photons undergo before detection, and the losses at the scintillator/photodetector boundary due to index of refraction mismatches, only a fraction of the original scintillation light created is available for detection at the photodetector 48. Reflective coatings are typically applied to all surfaces of the crystal 11 with the exception of the bottom end 32 where the photodetector 48 is applied.

Figure 4:
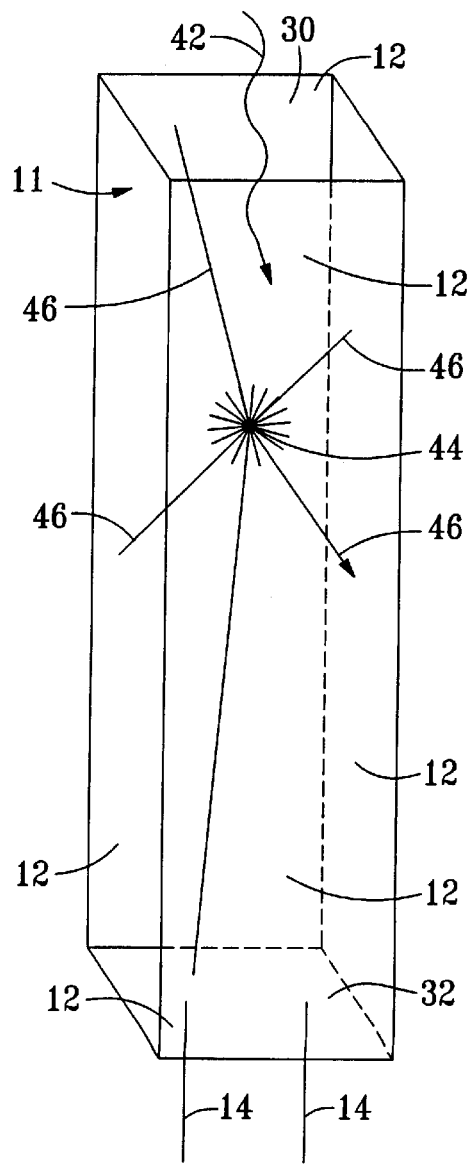
FIG. 4 is a schematic transparent representation of a single scintillation crystal of FIG. 1 embodying features of the invention for reading the level of photons generated within the scintillating crystal.

In contrast to the prior art depicted in FIG. 3, FIG. 4 is a schematic representation of a single scintillating crystal 11 utilizing features of the invention. Rather than utilizing reflective coatings on all surfaces, a photodetector 12 is formed on at least one long surface of the crystal 11 thereby eliminating or reducing the use of reflective coatings. FIG. 4 represents the use of photodetector 12 applied to all surfaces. As in the prior art, optical photons 46 are created from gamma-ray 47 interaction 44 within the crystal 11. However, when all surfaces of the crystal 11 are coated with a photodetector 12, all photons striking the wall are seen by the SPD. Ideally, for maximum signal detection, the number of photodetecting surfaces in a given crystal will be optimized and the number of reflections minimized. The leads for detecting the SPD output 14 are at the bottom of the crystal 11. Means 104 for recording scintillation radiation are connected thereto. Even if only one side face of the long, narrow crystal is covered by the SPD, the number of reflections photons undergo and the average path lenght before hitting that side is still greatly reduced, and the resulting light signal increased, compared to end readout.

Figure 6:
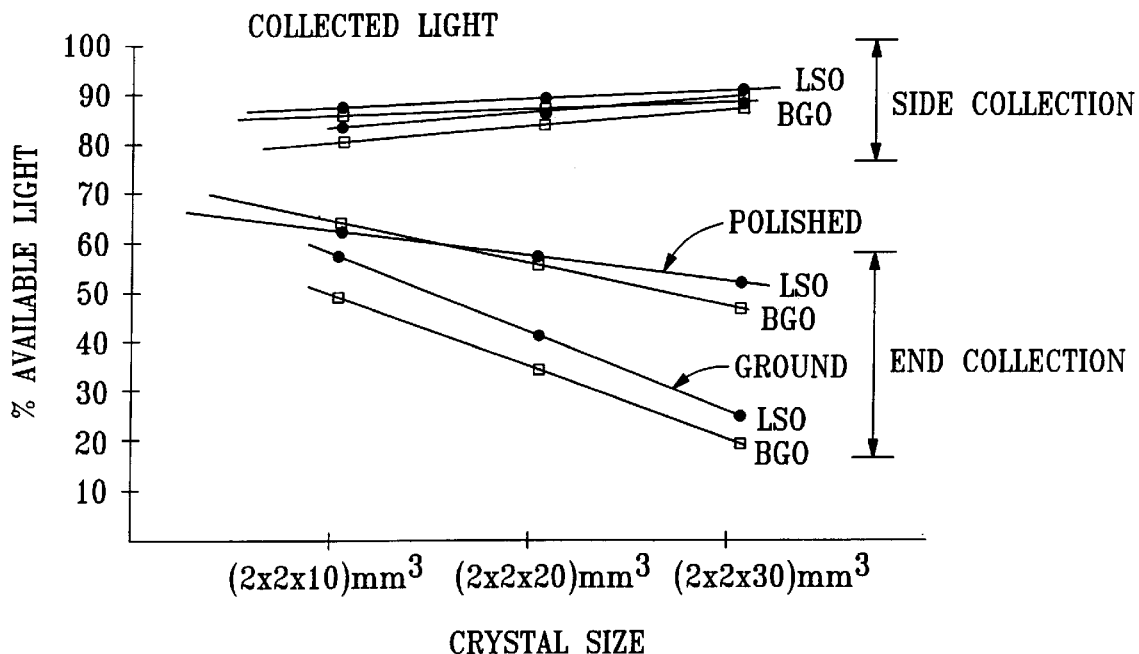
FIG. 6 is a graph illustrating the improved efficiency of collection of photons generated within a crystal embodying features of the invention.

FIG. 6 illustrates that side collection of light from a scintillating crystal is more efficient than the conventional end collection method. The amount of light detected from one long side of a Lutetium Oxyorthosilicate (LSO) or Bismuth Germanate (BGO) scintillation crystal as shown in FIG. 6 approaches 90% of the available light created. A conventional photodetector design coupled to one end of a scintillating crystal detects at best 64% of the photons created and the light collection is dependent upon such variables as crystal, length, width, size, and whether the long surfaces of the crystal have been polished. Because of the increased amount of light measured by and the compact nature of devices incorporating the invention, such a crystal array has the ability to yield a higher spatial resolution image with better contrast and improved counting efficiency because of an improved light collection efficiency.

Comparison of light collected for single side (long face) and end (small face) readout schemes for 3 sizes and 2 surface treatments of LSO and BGO crystals. Values shown are % of available light collected.

TABLE 1

| Readout/Surfaces | 2 × 2 × 10 mm³ | | 2 × 2 × 20 mm³ | | 2 × 2 × 30 mm³ | |
| --- | --- | --- | --- | --- | --- | --- |
| | LSO | BGO | LSO | BGO | LSO | BGO |
| End/Polished | 61.9 | 63.8 | 55.3 | 53.1 | 50.0 | 44.6 |
| Side/Polished | 89.9 | 87.1 | 90.6 | 88.9 | 91.4 | 88.3 |
| End/Ground | 58.5 | 49.8 | 37.7 | 31.1 | 23.9 | 19.1 |
| Side/Ground | 86.7 | 83.2 | 88.3 | 83.0 | 89.0 | 83.3 |

Optical photon tracking Monte Carlo simulations were performed to determine light output characteristics for BGO and LSO scintillation crystals for various readout conditions. Assumptions were made that a gamma-ray interaction within the crystal will generate a single point source of light at various depths and that the crystal surfaces without the photodetector mounted thereto are polished and coated with a material that is 98% reflective.

Table 1 summarizes the results from the simulations of light collected. Light collected in 2×2×10, 2×2×20, and 2×2×30 mm crystals was studied with both end face (2×2 mm area) and one large face (2×10, 2×20 and 2×30 mm, respectively) readout of the scintillation light. For each case, both perfectly polished and highly ground surface treatment results are shown. In reality, it may only be possible to achieve surfaces somewhere between these idealized treatments. The values in the table are the average fraction (%) of the total available light collected. The average was calculated over several origins of the source of the light (depths of interaction) within a crystal by weighing the location of the origin with the interaction probability at that location.

The data from Table 1 is also plotted in FIG. 6. From Table 1 and FIG. 6, we see that the light collection fraction is relatively insensitive to crystal length and surface treatment when one side (large face) readout is used. In addition, for a series of simulations performed with narrower (<2 mm wide) crystals and side readout, the light collected was fairly independent of crystal width. Thus, side readout opens the possibility of reducing the width of the crystals below 2 mm and, thus, improving intrinsic spatial resolution while still collecting a high fraction of the available scintillation light. In fact, because of the increase in SPD noise with larger total area, this scheme favors very narrow crystals. In contrast thereto using end readout, the predicted light collection strongly depends on the crystal length, width and surface conditions. A related effect is that the amount of light collected depends on where within the crystal the radiation interacted relative to the photodetecting end.

The clear improvement in the amount of scintillation light collected for side compared to end readout is readily apparent from FIG. 6. The improvement is huge when the crystal is ground ("lossy") and significant even when the crystal surface is perfectly polished. The improvement is also greater for longer crystals, due to the larger number of reflections photons undergo before exiting a crystal for end compared to side face readout. For perfectly polished crystals (the ideal case), the predicted improvement of side over end readout of the scintillation light is roughly 45, 64 and 83% for the 2×2×10, 2×2×20, 2×2×30 mm size LSO crystals, respectively. For narrower (<2 mm) crystal widths simulated, these differences were larger.

The large advantage of side over end readout becomes most evident for less polished crystals. For 2×2×10, 2×2×20, and the 2×2×30 mm size ground crystals, the predicted improvement in light collected on the crystal side when compared to end readout is, respectively, 48, 120 and 272% for LSO, and 67, 167, and 336% for BGO. These results are highly significant because perfectly polished crystals are expensive and not readily available and the difference in light collected between the two surface treatments is not significant for side readout of the scintillation light. For all crystal lengths and widths studied, using the side readout, the fraction of available light collected was greater than 90% for highly polished LSO crystal surfaces and greater than 87% for ground LSO crystal surfaces.

Figure 8A:
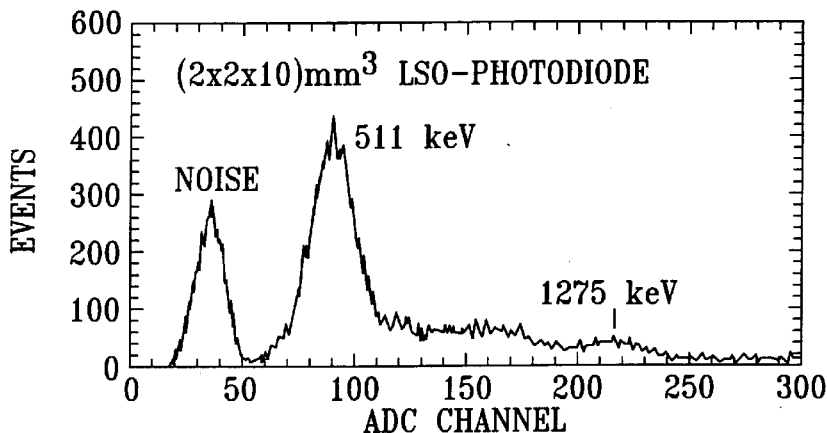
FIG. 8a is a graph showing the Na-22 pulse height spectrum for single side readout with a 3×30 mm silicon photodiode on a 2×2×10 mm LSO crystal with polished surfaces.
Figure 8B:
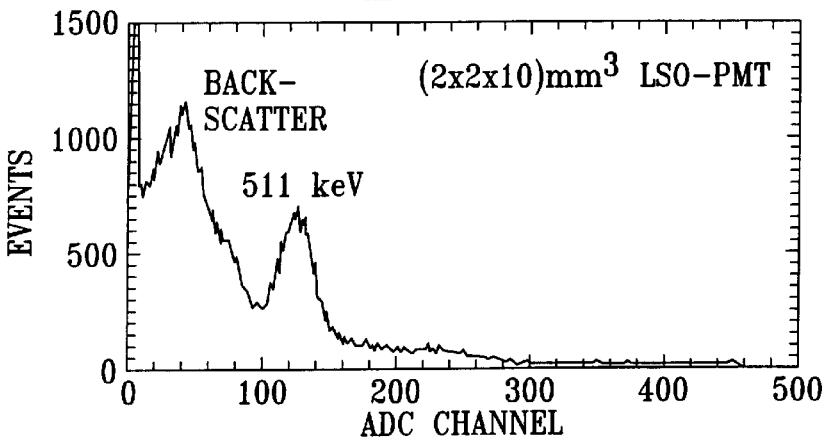
FIG. 8b is a graph showing the pulse height spectrum for end readout with a PMT on a 2×2×10 mm LSO crystal with polished surfaces.
Figure 9A:
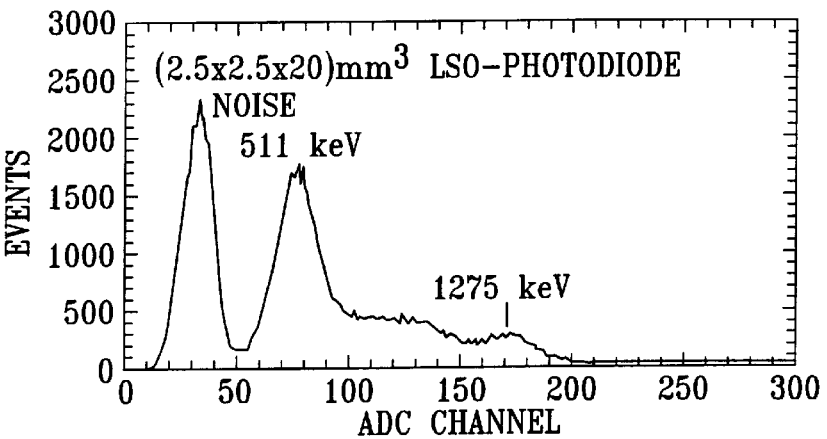
FIG. 9a is a graph showing the pulse height spectrum for single side readout with a 3×30 mm silicon photodiode on a 2.5×2.5×20 mm LSO crystal with polished surfaces.
Figure 9B:
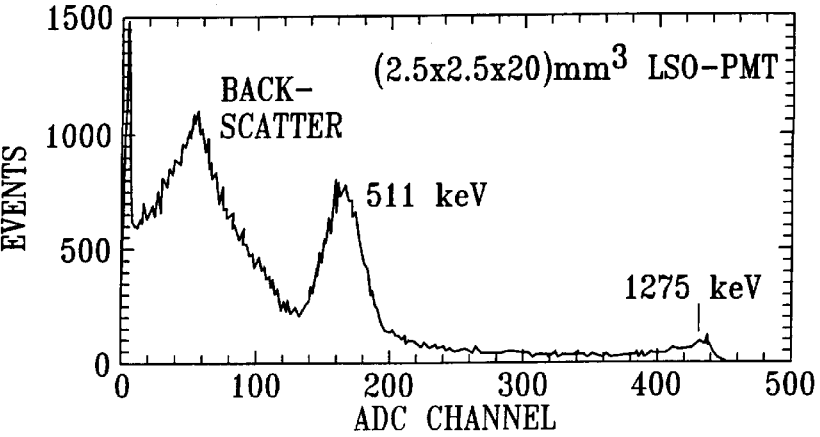
FIG. 9b is a graph showing the pulse height spectrum for end readout with PMT on a 2.5×2.5×20 mm LSO crystal with polished surfaces.
Figure 10A:
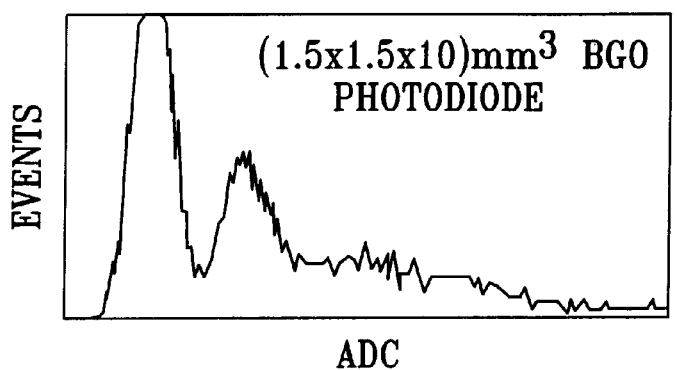
FIG. 10a is a graph showing pulse height spectrum for single side readout with a 3×30 mm silicon photodiode on a 1.5×1.5×10 mm BGO crystal with ground surfaces.
Figure 10B:
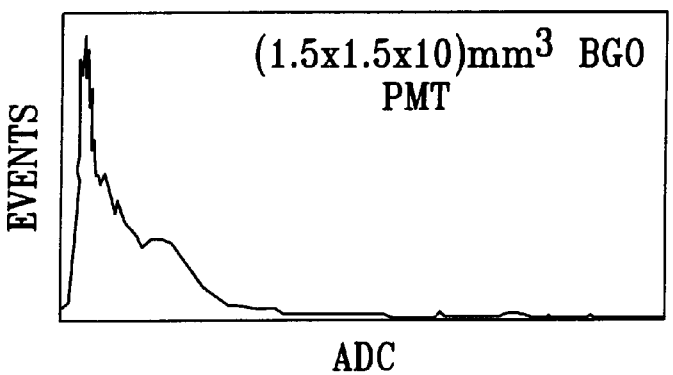
FIG. 10b is a graph showing pulse height spectrum for end readout with a PMT on a 1.5×1.5×10 mm BGO crystal with ground surfaces.
Figure 11A:
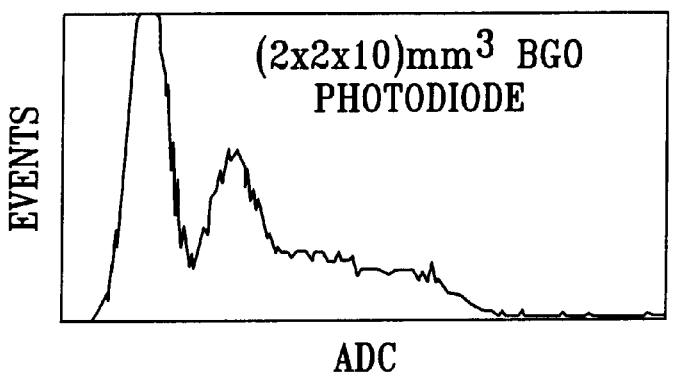
FIG. 11a is a graph showing pulse height spectrum for single side readout with a 3×30 mm silicon photodiode on a 2×2×10 mm BGO crystal with polished surfaces.
Figure 11B:
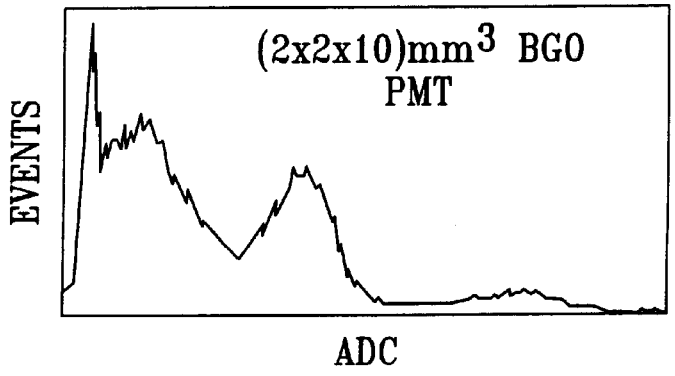
FIG. 11b is a graph showing pulse height spectrum for end readout with a PMT on a 2×2×10 mm BGO crystal with polished surfaces.
Figure 12A:
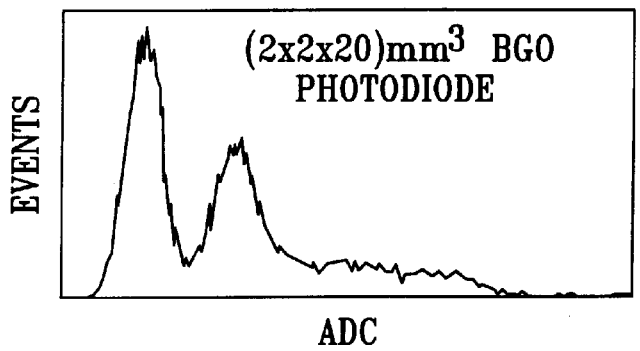
FIG. 12a is a graph showing pulse height spectrum for single side readout with a 3×30 mm silicon photodiode on a 2×2×20 mm BGO crystal with partially polished surfaces.
Figure 12B:
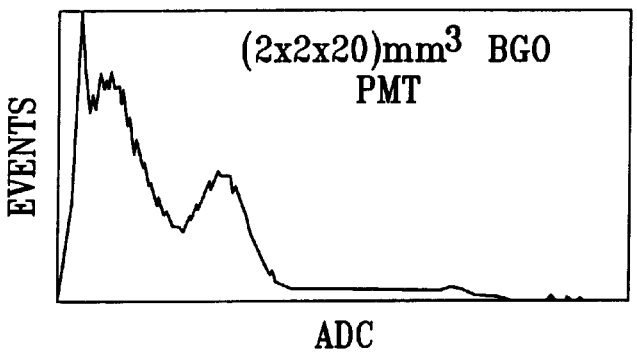
FIG. 12b is a graph showing pulse height spectrum for end readout with a PMT on a 2×2×20 mm BGO crystal with partially polished surfaces.
Figure 13A:
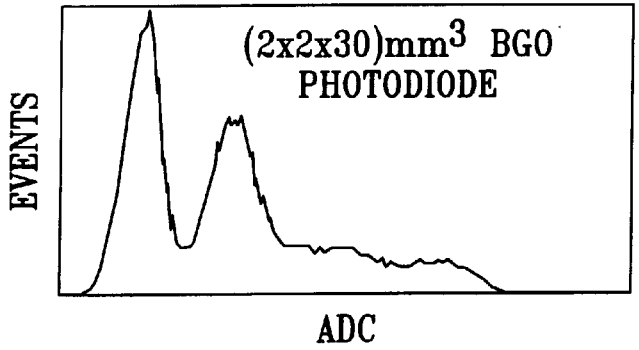
FIG. 13a is a graph showing pulse height spectrum for single side readout with a 3×30 mm silicon photodiode on a 2×2×30 mm BGO crystal with partially polished surfaces.
Figure 13B:
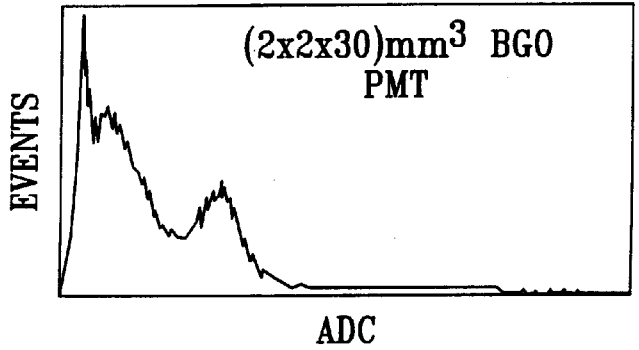
FIG. 13b is a graph showing pulse height spectrum for end readout with a PMT on a 2×2×30 mm BGO crystal with partially polished surfaces.

To ascertain whether the photodetector readout scheme proposed has sufficient signal to noise ratio for PET, one important comparison to make is between energy measurements performed with scintillation crystals readout from the side face with a silicon photodiode compared to the end face with a PMT. FIGS. 8a and b and 9a and b compare the 2×2×10 mm and 2.5×2.5×20 mm sizes of LSO crystals. FIGS. 10a and b, 11a and b, 12a and b, and 13a and b are similar comparisons for 1.5×1.5×10 mm, 2×2×10 mm, 2×2×20 mm, and 2×2×30 mm size BGO crystals. A Na-22 source of 511 keV gamma-rays was used for all measurements shown.

The spectroscopy amplifier gain used for the PMT data in FIGS. 8–13 was approximately twice that used for the photodiode. To facilitate comparisons, all photodiode spectra presented have the same amplifier gain and ADC channel scale on the plots. The same is true for all PMT spectra. The measured energy resolution of the 511 keV photopeak from $^{22}$Na was 24% FWHM for both the photodiode side and PMT end readout using the 2×2×10 mm LSO crystal. For the 2.5×2.5×20 mm LSO crystal, the corresponding values were 23% for the photodiode and 21% for the PMT. Even though the PMT gain is higher and the noise current is lower than for the photodiode, with PMT end face readout of the crystal there is no significant signal to noise ratio gain over the photodetector side face readout for these narrow LSO crystals. This is the case since only a small fraction of the available scintillation light is collected with end readout.

In addition, as predicted by the simulations, the photodiode results for pulse height (photopeak position) and energy resolution (photopeak width) are fairly insensitive to the length and width of the crystal. However, because of the higher noise shoulder of the photodetector seen in FIGS. 8–13b, the lower energy scatter continuum is not resolved ("in the noise"). It was found that the 511 keV photopeak energy resolution measured for larger LSO crystals with a much higher width to length ratio showed significantly improved results. For example, for a 4×4×10 mm$^3$ LSC crystal, 14% FWHM was obtained at 511 keV.

It should also be noted that the sensitive area of the photodetector (3×30 mm$^2$) used for the spectral measurements was much larger than required to read out either the 2×2×10 mm$^3$ or 2.5×2.5×20 mm$^3$ LSO samples from the side. With a smaller photodiode area, the noise component would be reduced, and the photodiode energy resolution measurements would improve.

The design as shown in FIG. 7, where light is received by SPDs on two long surfaces of the crystal, may be more efficient than the single surface side collection shown in FIG. 5. However, the larger the total area of the SPD used, the higher the device noise level for each crystal.

The SPD in this concept can be any type of material that can be fabricated directly on the detector, although ideally, the absorption spectrum of the photodetector should match the emission spectrum of the scintillation crystal as closely as possible. One example is a semiconductor silicon P-I-N photodiode with quantum efficiency enhanced for blue light sensitivity. The SPD should be as thin as possible to reduce the amount of gamma-ray insensitive material (i.e. dead area) between crystals receiving emissions from the patient. By using the scintillation crystal as the substrate for the deposition of the photodetector, or by stripping the silicon from its substrate, dead area regions are minimized. In the former case, optically conductive adhesives are not required. In FIG. 4 conducting leads 14 for bias, ground and electronic readout are preferably configured on or adjacent to the bottom of each scintillation crystal.

The resultant signal from the entire SPD "cover" or partial cover is then used to determine the crystal of interaction. The signals from the crystals in an array, after initial pre-amplification electronics, can be read out in parallel, or possibly capacitive or resistive charge division may be used to reduce the net number of channels required for positioning of an event. The crystal in the array that produces a signal above the inherent electronic noise is the gamma-ray crystal of interaction, which helps to identify the original direction of propagation of this gamma-ray leaving the patent's body. Determining the direction of propagation of a large number of gamma-ray, emanating from the patient's body for multiple scintillation crystal array positions and views results in an image of the original radio-isotope distribution as in the standard NMI mode practices.

Although the present invention has been described in considerable detail with reference to certain preferred versions and uses thereof, other versions and uses are possible. For example, while silicon photodiodes have been suggested, one skilled ill the art would recognize that other inorganic or organic based photodetectors are suitable for the use in the designs disclosed herein. Therefore, the spirit and scope of the appended claims should not be limited to the description of the preferred versions contained herein.

What is claimed is:

1. A gamma ray radiation device, comprising at least one scintillation crystal each said crystal generating scintillation radiation as gamma radiation passes therethrough having at least one long, narrow surface, at least one said long narrow surfaces being coated with a semiconductor photodetecting device, a means for recording scintillation radiation being connected thereto, greater than about 80% of the scintillation radiation generated being detected by the photodetecting device.

2. The gamma ray radiation detection device of claim 1 where all of said long narrow surfaces are coated with a semiconductor photodetecting device.

3. The gamma ray radiation detection device of claim 2 further having means to determine the position of scintillation light created by interaction with each scintillation crystal.

4. The gamma ray radiation detecting device of claim 1 consisting of a continuous crystal with one face covered by a pixillated pattern of semiconductor photodetectors formed directly on the crystal, said pixillated pattern functioning as the semiconductor photodetecting device.

5. The gamma ray radiation detection device of claim 1 further having means to determine the position of scintillation light created by interaction with the crystal.

6. The gamma ray detection device of claim 1 wherein the crystal has a long narrow surface which is at least 10 mm in length and equal to or less than about 2 mm in width.

7. The gamma ray detection device of claim 1 wherein the crystal has a long narrow surface which is at least 30 mm in length and equal to or less than about 2 mm in width, about 90% of the scintillation radiation generated being detected by the photodetecting device.

8. A gamma ray radiation detection device, comprising an array of multiple scintillation crystals each said crystal generating scintillation radiation as gamma radiation passes therethrough wherein each crystal in said array has at least one long narrow surface, at least one long narrow surface on each scintillation crystal being coated with a semiconductor photodetecting device, a means for recording scintillation radiation being connected to each crystal, greater than about 80% of the scintillation radiation generated being detected by the semiconductor photodetecting device.

9. The gamma ray radiation detection device of claim 8 wherein all of said long narrow surfaces are coated with the semiconductor photodetecting device.

10. The gamma ray radiation detection device of claim 9 further having means to determine the position of scintillation light created by interaction within each scintillation crystal.

11. The gamma ray radiation detection device of claim 8 further having means to determine the position of scintillation light created by interaction within each scintillation crystal.

12. The gamma ray detection device of claim 8 wherein each crystal has a long narrow surface which is at least 10 mm in length and equal to or less than about 2 mm in width.

13. The gamma ray detection device of claim 8 wherein each crystal has a long narrow surface which is at least 30 mm in length and equal to or less than about 2 mm in width, about 90% of the scintillation radiation generated being detected by the photodetecting device.

14. A gamma ray radiation detection device comprising an array of scintillation crystals, and means for detecting photons generated in said scintillation crystals, comprising multiple rows of parallel disposed elongated crystals and a plurality of substrate panels, one of said substrate panels being disposed between respective rows of said scintillation crystals, each of said panels having a plurality of photodetectors mounted thereon, each photodetector being paired with and aligned with a scintillation crystal to act to receive the light generated only from said crystal, the alternating rows of parallel elongated crystals and substrate panels forming an array of crystals disposed to intercept gamma radiation emanating from a target, the array of multiple rows of scintillation crystals with photodetectors capturing greater than about 80% of the scintillation generated photons.

15. The gamma ray radiation detection device of claim 14 further having means to determine the position of scintillation light created by interaction within each scintillation crystal.

16. In a scintillation camera for radioisotope imaging employing an array of scintillation crystals, an array of photodetectors in optical communication with said scintillation crystals, the photodetectors generating electrical signals which provide position information with regard to the location of scintillation generated photons occurring in said scintillation crystal in response to incident gamma radiation, electrical circuitry connected to said photodetectors for receiving electrical signals from said photodetectors and for producing composite image signals, and an image representation means for receiving said image signals and depicting signals for a single detected radioactive event as position coordinates of interaction of said event with the aforesaid crystal, the improvement comprising capturing at least about 80% of the photons generated by scintillation by at least partial encapsulation of each of said scintillation crystals within a respective photodetector.

17. The gamma ray detection device of claim 16 wherein each crystal has a long narrow surface which is at least 10 mm in length and equal to or less than about 2 mm in width.

18. The gamma ray detection device of claim 16 wherein each crystal has a long narrow surface which is at least 30 mm in length and equal to or less than about 2 mm in width, about 90% of the scintillation radiation generated being detected by the photodetecting device.

* * * * *